United States Patent
Putnam et al.

[11] Patent Number: 5,230,352
[45] Date of Patent: Jul. 27, 1993

[54] MEDICAL SUTURING DEVICE, A SINGLE-STRIKE DIE MECHANISM, AND A METHOD OF USING SAID DIE MECHANISM FOR FORMING THE MEDICAL SUTURING DEVICE

[75] Inventors: Charles L. Putnam, West Redding; Mark L. Stein, Bethel, both of Conn.; Patrick R. Holmes, Nr Southampton, England

[73] Assignee: American Cyanamid Company, Stamford, Conn.

[21] Appl. No.: 846,456

[22] Filed: Mar. 4, 1992

[51] Int. Cl.$^5$ .............................................. A61B 17/32
[52] U.S. Cl. .................................. 128/898; 606/226; 606/224; 223/102; 163/1
[58] Field of Search ............... 606/222, 224, 225, 226; 163/1; 223/102; 29/520, 515, 505, 709, 715, 283.5; 128/898

[56] References Cited

U.S. PATENT DOCUMENTS

| | | | |
|---|---|---|---|
| 3,416,352 | 12/1968 | Ribback | 72/402 |
| 3,733,883 | 5/1973 | Kaczmarek | 72/402 |
| 4,041,766 | 8/1977 | Johnson et al. | 72/402 |
| 4,072,041 | 2/1978 | Hoffman et al. | 72/416 |
| 4,306,443 | 12/1981 | Matsutani | 72/434 |
| 4,722,384 | 2/1988 | Matsutani | 163/1 |
| 4,799,311 | 1/1989 | Matsutani | 29/709 |
| 4,806,737 | 2/1989 | Coates | 219/390 |
| 4,832,025 | 5/1989 | Coates | |
| 4,922,904 | 5/1990 | Uetake et al. | 606/226 |
| 5,099,676 | 3/1992 | Proto et al. | 72/416 |

FOREIGN PATENT DOCUMENTS

| | | | |
|---|---|---|---|
| 1022734 | 12/1977 | Canada | 26/83 |
| 3539891 | 11/1986 | Fed. Rep. of Germany | 606/224 |

Primary Examiner—Stephen C. Pellegrino
Assistant Examiner—Jeffrey A. Schmidt
Attorney, Agent, or Firm—Charles F. Costello, Jr.

[57] ABSTRACT

A single-strike die mechanism includes a rotatable cam drive ring driven to impart through a cam mechanism linear motion to at least three crimping dies. The crimping dies are symmetrically arranged within a die guide and simultaneously actuated to move in a radial direction toward a centerline of a surgical needle. A surgical suture is axially inserted within a hollow barrel end of the needle, and the barrel end is crimped by the crimping dies to secure the suture therein. A method for operating the single-strike die mechanizes the procedure for securing the suture within the barrel end of the needle.

10 Claims, 5 Drawing Sheets

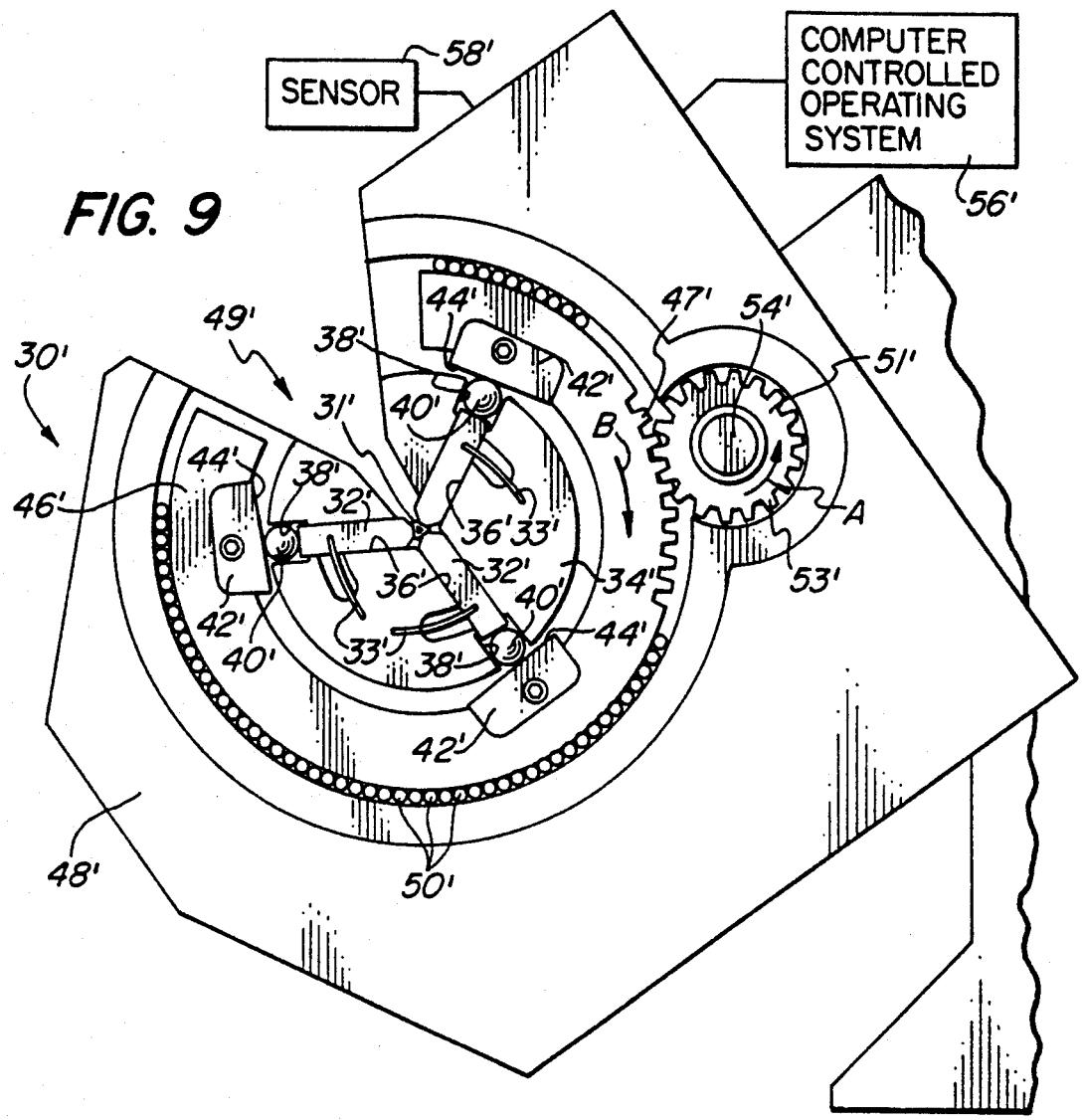

MEDICAL SUTURING DEVICE, A SINGLE-STRIKE DIE MECHANISM, AND A METHOD OF USING SAID DIE MECHANISM FOR FORMING THE MEDICAL SUTURING DEVICE

BACKGROUND OF THE INVENTION

1. Field of the Invention

The present invention relates to single-strike die and a method for using the die to produce a medical suturing device. More particularly, the present invention relates to a single-strike die and a method for using the die to attach a surgical suture to a surgical needle.

2. Description of the Prior Art

The medical procedure of suturing by hand a surgical or other wound in tissue or organs involves the use of a surgical needle with a surgical suture attached thereto. For simplicity, reference will be made hereafter only to suturing of tissue.

Typically, the needle punctures the tissue from the outside on one side of the wound, traverses across the wound and then punctures the tissue from the inside on the other side of the wound, pulling the suture through these punctured openings. The suture is then tied-off to form a single suture, or stitch, and to close the wound between the punctured openings. This procedure is repeated along the length of the wound. The needle is usually curved to make it easier to push through both sides of the tissue and includes a sharpened tip at its lead or distal end and a hollow barrel at its trailing or proximal end, which is hollow by virtue of being formed with a blind axial hole. The suture is axially inserted into the hollow end and secured in the barrel. It is important to tightly secure the suture within the barrel so it does not loosen and become separated from the needle during the hand-suturing procedure.

The art of attaching a surgical suture to the barrel of a surgical needle has been practiced for many years. One conventional method that has been practiced uses two opposing dies that are machined to have end profiles which complement the shape and diameter of the barrel of the needle. U.S. Pat. Nos. 4,306,443; 4,722,384; and 4,799,311 relate to crimping apparatus of this type. With the suture inserted into the hollow barrel of the needle, one die moves relative to the other to crimp the barrel at one location about its periphery. After the first crimping operation, the needle is manually rotated and a second and sometimes a third crimping operation is performed to securely crimp the suture within the barrel of the needle. However, several drawbacks associated with this method, such as the time consumed in performing several crimping operations and the imprecision of choosing the locations on the barrel to be crimped, make this an unsatisfactory procedure.

Another conventional method for attaching a surgical suture to the hollow barrel of a surgical needle involves the use of a single-strike die. The die is so named because it crimps the barrel of the needle in a plurality of locations in a single crimping procedure. Canadian Patent No. 1,022,734 shows such a single-strike die for securing a suture to a surgical needle. Two dies are used to perform the crimping, or swaging, procedure. In one example, each die is machined to have a die profile with two flat faces formed at a 90° angle to one another thereby to define a V-shaped notch. As the dies are compressed about the suture-containing needle barrel, the needle is crimped at four radial locations about the barrel. Another example shows one die with a flat face and a second die with a V-shaped opening that together crimp the suture-containing needle at three locations about the barrel. However, the multi-faceted profiles of these dies are expensive to machine. Moreover, these die profiles are machined to fit specific barrel diameters. Therefore, the dies must be changed if needles with barrels of a different diameter are to be crimped.

Conventional methods for securing surgical sutures to surgical needles also suffer from requiring too much manual input from the machine operators. Throughout a working day, repeated turning of the needle between crimps, or manually regulating the crimping pressure of the machines, which often use pneumatic drive systems or electrically powered cam-actuated drive systems, can reduce the speed and efficiency of producing suture-containing needles. Still further, requiring the operator to determine the locations on the barrel to be crimped or the amount of pressure to be applied to the needle leads to inconsistent quality and inferior suture-containing needles and increases the failure or rejection rate. For example, if the barrel of the needle is not crimped at enough locations or the locations are not properly spaced around the barrel, the suture can slip out of the barrel during the hand-suturing procedure. In addition, if the operator regulates the conventional dies to apply too much pressure to the barrel it may crack and in such case the needle will have to be discarded.

Accordingly, further improvements and advances in single-strike dies, methods of using single-strike dies to provide medical suturing devices, and medical suturing devices comprising surgical needles with securely attached surgical sutures are needed.

SUMMARY OF THE INVENTION

Accordingly, it is a principal object of the present invention to provide an improved single-strike die and method for using that die to produce a medical suturing device.

It is an object of the invention to provide a single-strike die for efficiently and precisely securing a surgical suture to a surgical needle.

It is a further object of the invention to provide a method of operating the single-strike die to mechanize the process of securing a surgical suture to a surgical needle.

It is still another object of the invention to provide a superior medical suturing device having a surgical needle with a surgical suture secured therein.

In accordance with one aspect of the present invention, a medical suturing device comprises a surgical needle having a pointed leading end and a trailing barrel end, with a surgical suture axially inserted in the barrel end. The barrel end is compressed about its circumference at a plurality, for example, three, symmetrical locations to provide indentations for securing the suture therein.

In accordance with another aspect of the present invention, a single-strike die mechanism for securing a surgical suture to a barrel of a surgical needle comprises a cam drive ring, having a radial opening, mounted for rotational movement about a central axis, cam drive ring mounting means for rotationally mounting the cam drive ring, and drive means for rotating the cam drive ring. A plurality of crimping dies are mounted for movement in a radial direction with respect to the central axis, and a die guide symmetrically mounts each of the plurality of crimping dies for linear movement in the radial direction. In addition, actuating means linearly actuate the plurality of crimping dies in the radial direction.

In accordance with still another aspect of the present invention, a method of producing a medical suturing device by use of a single-strike die having a plurality of crimping dies comprises the steps of positioning the crimping dies generally to form a circumscribed circle larger in diameter than the barrel end of a surgical needle, inserting the needle within the circumscribed circle, and closing the crimping dies to a gripping position for lightly gripping the barrel to secure the needle but so as not to deform the barrel. A surgical suture is then axially inserted into the barrel and the crimping dies are further closed simultaneously to apply a crimping force to deform the barrel. The crimping dies are opened slightly to a testing position which releases the crimping force but does not permit axial movement of the barrel. The medical suturing device is tested by applying a tensioning force to the suture, and if the device is satisfactory, the crimping dies are then further opened to release the medical suturing device.

These and other objects, aspects, features and advantages of the present invention will become apparent from the following detailed description of the preferred embodiments taken in conjunction with the accompanying drawings.

BRIEF DESCRIPTION OF THE DRAWINGS

FIG. 9 is a top plan view, similar to FIG. 6, of the second embodiment of the single-strike die mechanism in the closed position; and FIG. 10 is an isolated top plan view, similar to FIG. 7, of the second embodiment of the single-strike die mechanism in the closed position.

DESCRIPTION OF THE PREFERRED EMBODIMENTS

Figure 1:
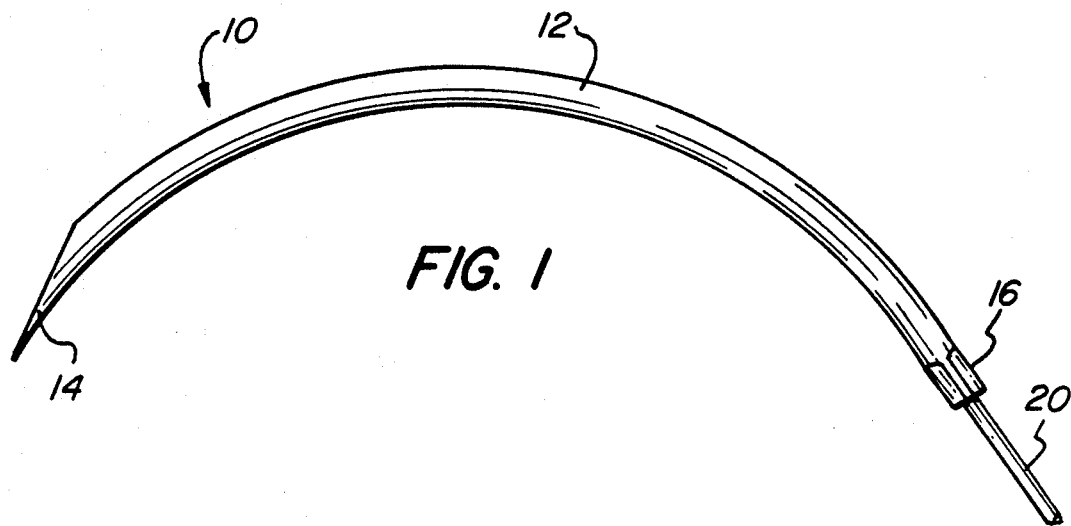
FIG. 1 is a side elevational view of a medical suturing device in accordance with the present invention.
Figure 2:
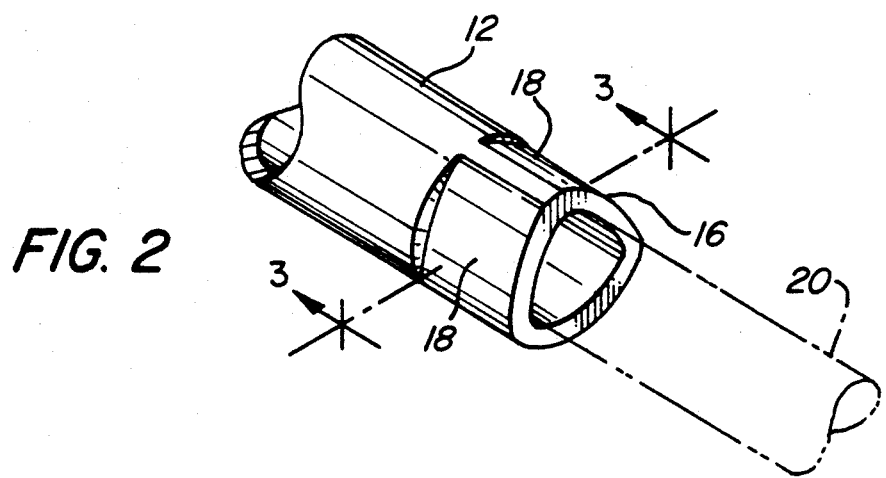
FIG. 2 is a partial perspective view of a barrel end of a surgical needle and a phantom view of a surgical thread attached to the needle barrel end.
Figure 3:
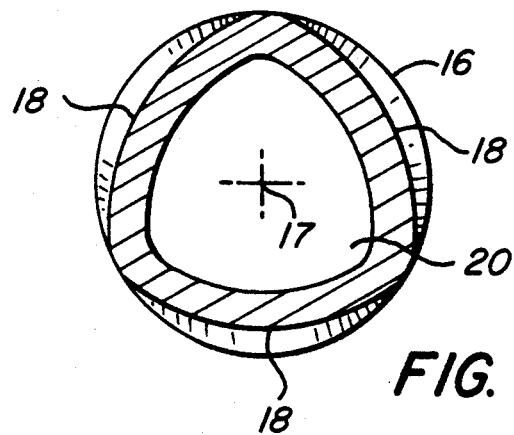
FIG. 3 is a cross-sectional view taken along plane 3—3 of FIG. 2, showing the crimped barrel end of the surgical needle.

FIGS. 1 through 3 illustrate a medical suturing device 10 in accordance with the present invention. The suturing device comprises a surgical needle 12 curved in a conventional manner and having a pointed forward or distal end 14 for piercing the tissue and a trailing, proximal hollow barrel end 16 formed by having a blind axial hole therein. A surgical suture 20 is axially inserted into the hollow barrel end to complete the device 10. The needle can be made, for example, of surgical grade stainless steel, and the suture can be made of either natural or synthetic material and consist of a monofilament or a multifilament braided structure as are known in the art.

FIGS. 2 and 3 show the hollow barrel end of the needle 12 and illustrate how the suture 20 is secured therein. With the suture axially inserted into the barrel 16, the wall of the hollow barrel end is deformed to form three radial indentations 18 that may be arcuate or convex as shown in detail FIG. 3, thereby being partially cylindrical having a radius greater than the radius of the major portion of the needle. Alternatively, the indentations may be substantial flat as described in greater detail below. Deforming the barrel wall reduces the internal diameter of the barrel and compresses, or squeezes, the suture so it is secured within the needle. In accordance with the present invention, the radial indentations are symmetrically spaced around the periphery of the barrel as shown in FIG. 3. Each indentation 18 is compressed toward a centerline 17 in the barrel 16 with the same force to apply three substantially equal forces to the suture through the barrel wall symmetrically about its circumference. It has been found that by using at least three symmetrically applied forces, the suture can be securely attached to the needle and will not become separated therefrom during the hand-suturing procedure. The apparatus and method for deforming the barrel of the needle 12 to secure the suture 20 therein are discussed below with reference to FIGS. 4 to 10.

Figure 4:
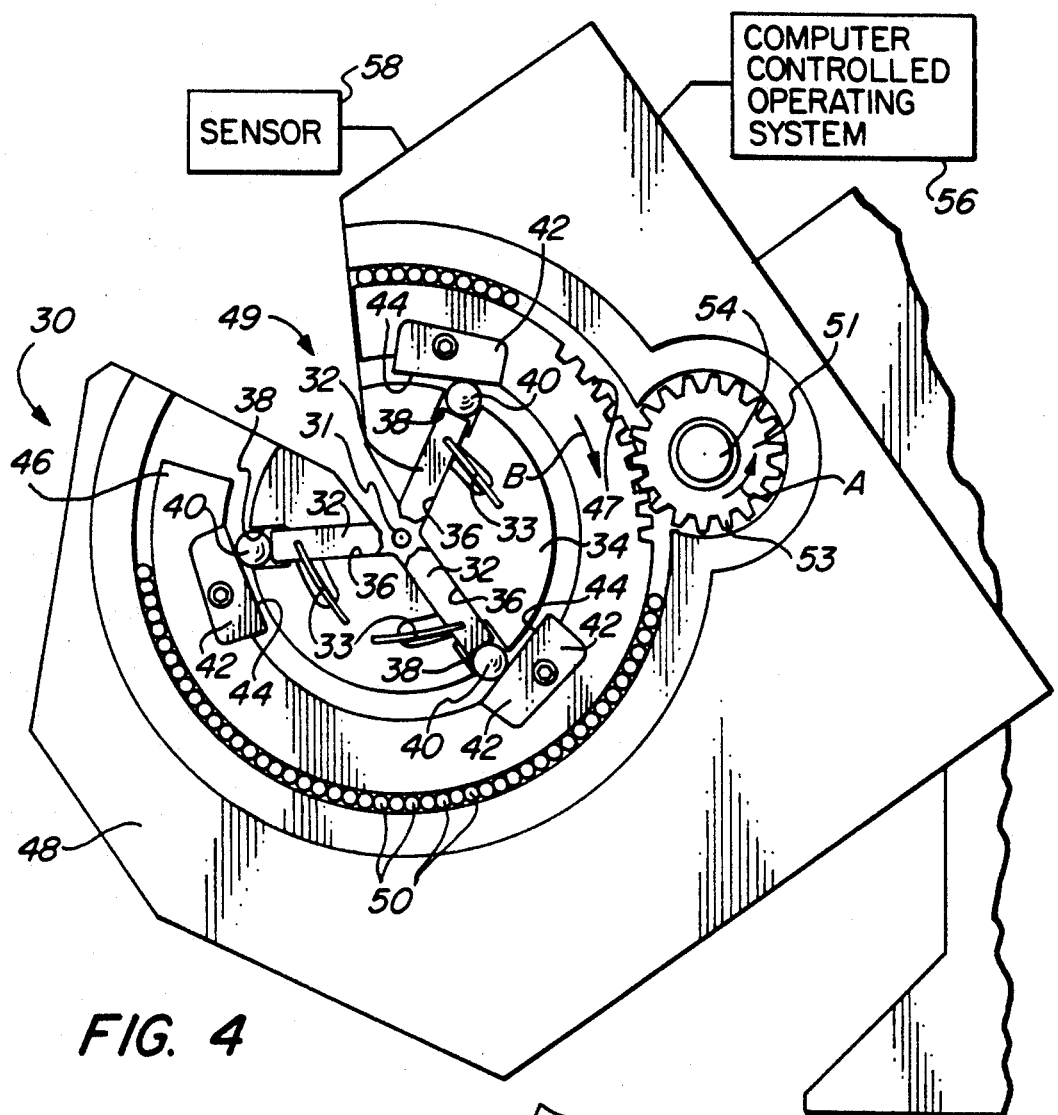
FIG. 4 is a top plan view of a single-strike die mechanism, in accordance with a first embodiment of the present invention, in an open position.
Figure 6:
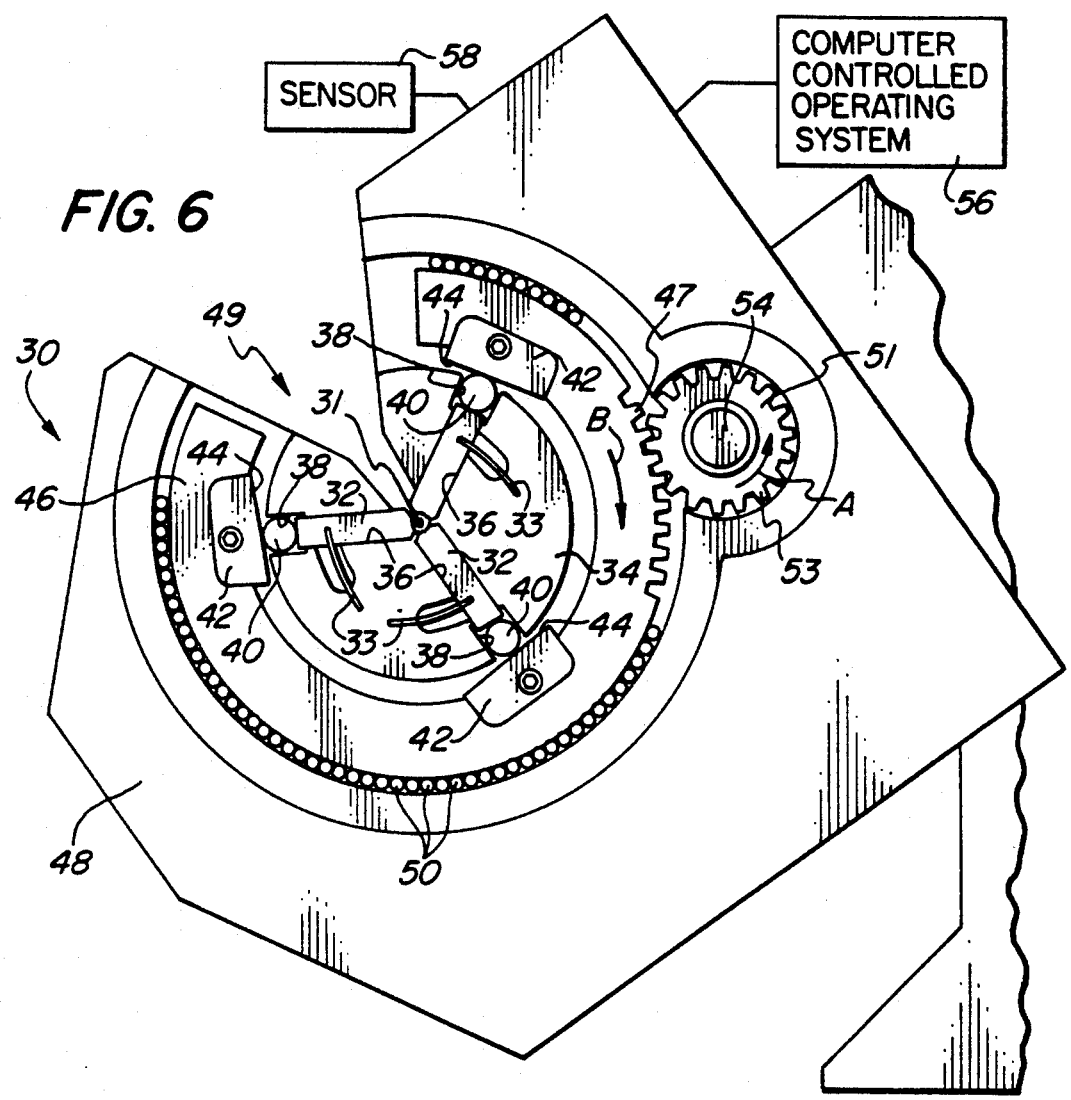
FIG. 6 is a top plan view of the single-strike die mechanism in a closed position.

A single-strike die mechanism 30, in accordance with a first embodiment of the present invention, for assembling the medical suturing device also in accordance with the present invention is best seen in FIGS. 4 and 6. The single-strike die mechanism 30 has a set of three crimping dies 32 supported for linear movement in a die guide 34. The crimping dies slide in a radial direction within symmetrically disposed paths 36 in the die guide, with each path having a wide-end portion 38 for reasons discussed below. As FIGS. 4 and 6 illustrate, the die guide 34 is substantially circular in shape, with the symmetrically disposed paths 36 being equally spaced 120° from each other and extending radially outwardly from a center axis 31 of the single-strike die. Leaf springs 33 are secured in the die guide and each urges one crimping die 32 radially outwardly from the center axis. Each crimping die is actuated through its association with a roller bearing 40 and a cooperating cam 42. Each roller bearing 40 is confined within the wide-end portion 38 of one path 36 between an angled camming surface 44 of one cam 42 and the opposed end of a crimping die 32.

The cams are positioned about the inner circumference of a cam drive ring 46, which in turn is supported for rotational movement within a drive ring housing 48. Ball or roller bearings 50 are positioned between the cam drive ring 46 and the drive ring housing 48 to provide smooth and precise rotational movement of the cam drive ring. A drive gear 51 rotates the cam drive ring through the meshing of its gear teeth 53 and a sector of gear teeth 47 on the drive ring 46. The drive gear 51 is connected to a drive shaft 54 which is driven by a motor (not shown).

Figure 5:
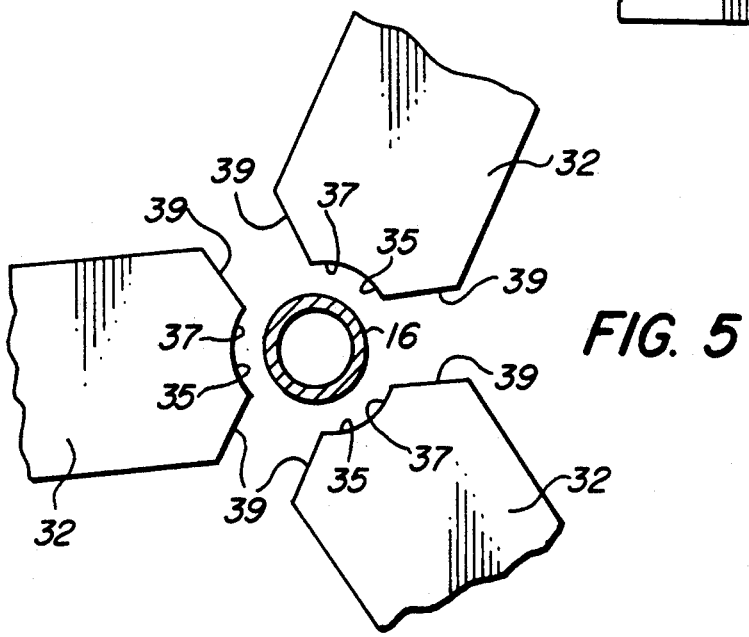
FIG. 5 is an isolated top plan view of the single-strike die mechanism in an open position.

Referring now to FIG. 5, it can be seen that each crimping die has a deforming face 35. Each deforming face 35 has a recessed arcuate or concave crimping surface 37 and laterally angled surfaces 39 at its leading end. The crimping faces in this embodiment desirably have a radius larger than that of the needle.

The operation of the single strike die mechanism 30 will now be explained with reference to FIGS. 4 through 7. When drive gear 51 is rotated in the counterclockwise direction, as indicated by arrow A, the cam drive ring rotates 46 in the clockwise direction, as indicated by arrow B, about the center axis 31. As the drive ring 46 rotates, the angled cam surfaces 44 force the roller bearings 40 confined in the wide-end portions 38 of the paths 36 radially inwardly. Each roller bearing, in turn, forces its associated crimping die 32 radially inwardly along one path 36. As will be appreciated, alternative camming systems which convert rotational movement of the cam drive ring into linear movement of the crimping dies are within the scope of this invention. Moreover, alternate driving systems, other than cam drive systems, that simultaneously drive each of the crimping dies radially inwardly are also within the scope of this invention.

The die guide and cam drive ring define a radial opening 49 that leads from the center axis 31 of the single-strike die to the outside of the drive ring housing. The mechanism 30 can be positioned so that the assembled suturing device may be removed through this radial opening 49 at the completion of an operating cycle of the single-strike die.

While the single-strike die mechanism 30 can be operated manually, a preferred embodiment of the invention includes a computer controlled operating system 56 and a sensor 58, as shown diagrammatically in FIGS. 4 and 6, to operate the single-strike die. The sensor 58 is used to sense the pressure with which a needle is gripped or deformed by the crimping dies and produces an output signal to which the computer controlled operating system 56 responds. Alternatively, the system 56 can be programmed to operate the mechanism 30 through its cycle described below based on such parameters as the diameter and material of the needle, the wall thickness of the hollow barrel end, the material and structure of the suture thread, and the lubricity of the surface of the suture inserted into the hollow barrel end. Still further, an additional sensor (not shown) can be adapted to sense the removal of a completed suturing device from the die mechanism to initiate a subsequent operating cycle.

While the components of the computer controlled operating system and sensor are conventional in and of themselves, their uniqueness lies in incorporation in the present invention and in the manner in which they operate the single-strike die mechanism to move the crimping dies through five positions during production of the medical suturing device shown in FIGS. 1 to 3.

More particularly, the production process starts with the crimping dies in an open position. The crimping dies are shown in FIG. 4 to be in that open position. The cam drive ring 46 is then rotated in the clockwise direction by the drive gear 51 to drive the crimping dies in radially inward directions to a needle inserting position. At this position, which is shown in FIG. 5, the surfaces 37 of the crimping dies generally circumscribe or define a circle of slightly larger diameter than the surgical needle. The surgical needle without the suture may then be guided to the location within the circumscribed circle.

The crimping dies 32 are thereafter again driven in the radially inward directions to a needle hold/suture insertion position. At this position, which can be seen in FIG. 6, the barrel end of the needle is gripped firmly to precisely align its centerline 17 with the central axis 31 of the single-strike die mechanism. However, under control of the computer controlled operating system 56, for example, which may respond to sensing by the sensor 58 of the gripping of the needle by the crimping dies, or which may be programmed directly to do so, the needle is gripped lightly enough so as not to deform the barrel. The surgical suture is then axially inserted into the barrel while the needle is held in this position.

Figure 7:
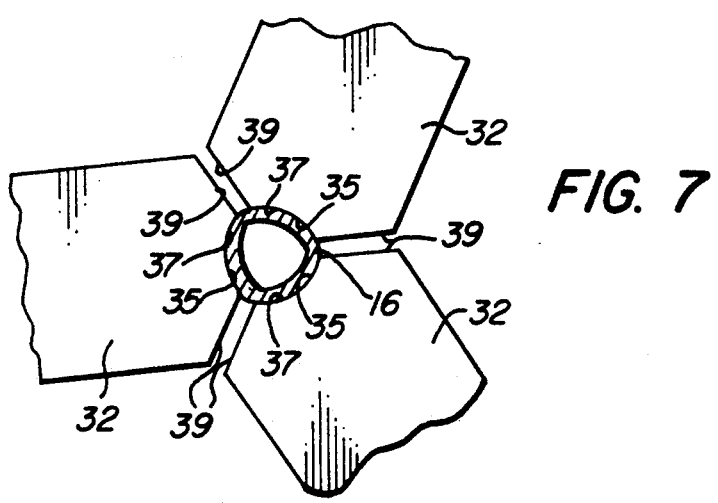
FIG. 7 is an isolated top plan view of the single-strike die mechanism in a closed position.

The crimping dies 32 are then driven further in the radially inward directions to deform the barrel and securely crimp the needle around the suture. As shown in FIG. 7, in this crimping position the barrel 16 is simultaneously compressed by crimping dies 32 at three symmetrical positions to crimp the suture within the barrel. When the crimping is completed, the direction of rotating the cam drive ring is reversed by reversing drive of the drive gear 51 and the crimping dies are then permitted to be urged in the radially outward directions by the force of the leaf springs 33. However, the crimping dies are first permitted to withdraw only slightly from the indentations formed in the barrel to a testing position. The circle generally circumscribed by the crimping dies in the testing position is smaller than the undeformed diameter of the barrel. Therefore, axial movement of the needle is prevented. In this position, a tensioning force is applied to the suture to attempt to remove it from the needle. This tensioning force is measured against a predetermined force value. If the suture remains crimped in the needle when the predetermined tensioning force is applied to the suture, it is judged that the suture is satisfactorily attached within the needle.

To complete the production cycle, the crimping dies are permitted to be urged further in the radially outward directions by the leaf springs by further counterclockwise rotation of the cam drive ring 46 again to be placed in the open position. The crimping dies thus completely release the suturing device in this position, and it may be removed from the single-strike die mechanism through the radial opening 49.

It will thus be appreciated that the configuration of the single-strike die mechanism in accordance with the present invention produces a needle-suture assembly quickly and efficiently, and in which the suture and needle are reliably secured together. In addition, the computer control of the single-strike die mechanism in accordance with the present invention enables the positions of the crimping dies to be controlled accurately to within tenths of thousandths of an inch. Thus, the single-strike die mechanism can continually and consistently produce reliable medical suturing devices. Still further, since the computer controlled operating system is operated by software, adjusting the single-strike die to accommodate needles of different diameters can be done almost instantaneously by regulating the positions of the crimping dies. This feature significantly reduces the amount of retooling of the crimping dies that must be done to accommodate needles of different diameters.

Figure 8:
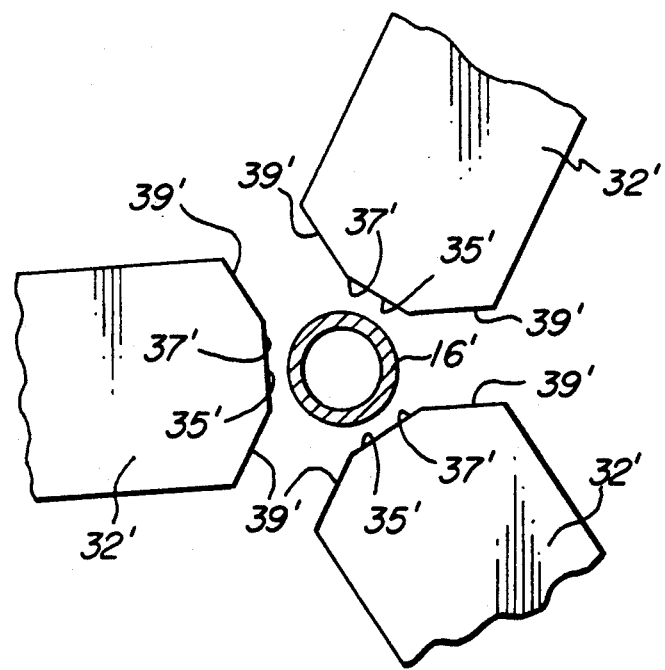
FIG. 8 is an isolated top plan view, similar to FIG. 5, of a second embodiment of the single-strike die mechanism in an open position.

A second embodiment of the single-strike die mechanism of the present invention is shown in FIGS. 8, 9 and 10. The components of this mechanism are identical to those of the first embodiments shown in FIGS. 5, 6 and 7 and as described above, with one-exception. Therefore, all reference numerals used in FIGS. 8, 9 and 10 are the same as those used in FIGS. 5, 6 and 7 but with the addition of a "prime".

The difference between the first and second embodiments is that in the second the crimping surface 37' on each deforming face 35' of each die 32' is flat, not concave. Therefore the second embodiment will produce three substantially flat, not convex, indentations in the hollow barrel end of the needle when it is crimped by the die mechanism. Thus, the convex surfaces 18 shown in FIGS. 2 and 3 will appear substantially flat as shown in FIGS. 9 and 10 when produced by the die mechanism of the second embodiment. This second configuration may be desirable when added crimping force is sought to be applied to the suture.

Although specific embodiments of the present invention have been described above in detail, it will be understood that this description is merely for purposes of illustration. Various modifications of and equivalent structures corresponding to the disclosed aspects of the preferred embodiments in addition to those described above may be made by those skilled in the art without departing from the spirit of the present invention which is defined in the following claims, the scope of which is to be accorded the broadest interpretation so as to encompass such modifications and equivalent structures.

What is claimed is:

1. A method of producing a medical suturing device, comprising the steps of:
    providing a single-strike die mechanism having a plurality of crimping dies each reciprocally movable in radially inward and outward directions, and each having a crimping surface that extends generally perpendicularly to the radial inward and outward direction;
    providing a surgical needle, having a hollow barrel end, and a separated surgical suture;
    positioning the crimping dies generally to define a circumscribed circle larger in diameter than the hollow barrel end of the surgical needle;
    inserting the needle within the circumscribed circle;
    closing the crimping dies in the radially inward direction to a gripping position for lightly gripping the barrel end;
    axially inserting the surgical suture into the hollow barrel end;
    further closing the crimping dies in the radially inward direction to apply a crimping force to deform the barrel end about the inserted surgical suture; and
    opening the crimping dies to release the surgical needle and attached suture.

2. A method of producing a suturing device according to claim 1, wherein the crimping force is applied symmetrically to the barrel end by the plurality of crimping dies.

3. A method of producing a suturing device according to claim 2, wherein the symmetrical crimping force is applied at three locations about the barrel end of the needle.

4. A method of producing a suturing device according to claim 1, further comprising the step of, after opening the crimping dies, releasing the surgical needle and attached suture through a radial opening in the single-strike die mechanism.

5. The method of producing a suturing device according to claim 1, wherein said closing step is performed in dependence on at least one of the diameter of the hollow barrel of the surgical needle and the material of the surgical needle.

6. The method of producing a suturing device according to claim 1, wherein said further closing step is performed in dependence on at least one of the diameter of the hollow barrel end of the needle, the wall thickness of the barrel end, the material of the needle, the material of the suture, the structure of the suture, and the lubricity of the surface of the suture inserted into the hollow barrel end.

7. The method of producing a suturing device according to claim 1, further comprising the step of sensing the force of said light gripping in said closing step thereby to prevent deforming said hollow barrel end of said needle during said closing step.

8. The method of producing a suturing device according to claim 1, further comprising the step of sensing the crimping force applied in said further closing step thereby to properly deform the barrel.

9. A method of producing a suturing device according to claim 1, further comprising the step, following said further closing step, of initially opening the crimping dies to a testing position, which releases the crimping force but does not permit axial movement of the barrel end at least in one direction.

10. A method of producing a suturing device according to claim 9, further comprising the step, following said initially opening step, of testing the suturing device by applying a tensioning force to the suture.

* * * * *